(12) United States Patent
Kleppen (10) Patent No.: US 9,757,219 B2
(45) Date of Patent: Sep. 12, 2017

(54) SUSPENDED MOTOR MOUNTING SYSTEM IN A POWER TOOTHBRUSH

(71) Applicant: KONINKLIJKE PHILIPS N.V., Eindhoven (NL)

(72) Inventor: Lane Evan Kleppen, Seattle, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/890,840

(22) PCT Filed: Feb. 18, 2015

(86) PCT No.: PCT/IB2015/051220
§ 371 (c)(1),
(2) Date: Nov. 12, 2015

(87) PCT Pub. No.: WO2015/159162
PCT Pub. Date: Oct. 22, 2015

(65) Prior Publication Data
US 2017/0020641 A1   Jan. 26, 2017

Related U.S. Application Data

(60) Provisional application No. 61/980,207, filed on Apr. 16, 2014.

(51) Int. Cl.
*A61C 17/34* (2006.01)
*A61C 17/22* (2006.01)
*H02K 7/14* (2006.01)
*H02K 33/00* (2006.01)

(52) U.S. Cl.
CPC ............ *A61C 17/34* (2013.01); *A61C 17/224* (2013.01); *H02K 7/14* (2013.01); *H02K 33/00* (2013.01)

(58) Field of Classification Search
CPC ........ A61C 17/34; A61C 17/22; H02K 33/00; H02K 7/14
USPC .......................................... 310/12–14, 49, 50
See application file for complete search history.

(56) References Cited

U.S. PATENT DOCUMENTS

| 2,278,365 | A | * | 3/1942 | Daniels | A61C 17/3427 |
| | | | | | 132/73.6 |
| 3,104,405 | A | | 9/1963 | Perrinjaquet | |
| 3,394,277 | A | * | 7/1968 | Lyons | A61C 17/40 |
| | | | | | 15/22.1 |
| 4,413,199 | A | | 11/1983 | Fischer | |
| 5,189,751 | A | | 3/1993 | Giuliani et al. | |
| 5,378,153 | A | | 1/1995 | Giuliani et al. | |
| 5,613,259 | A | | 3/1997 | Craft et al. | |

(Continued)

FOREIGN PATENT DOCUMENTS

CN   201676306 U   12/2010
CN   202143657 U   2/2012
(Continued)

*Primary Examiner* — Naishadh Desai (57) ABSTRACT

A system configured to mitigate axial shocks and rotational vibration in a resonating power toothbrush (10). The system includes a motor mount (70), frame (40), and multi-function coil bobbin (90) that act in concert to absorb axial shocks originating from the motor shaft (60). The mount (70), frame (40), and coil bobbin (90) also act in concert to damp vibrations originating from the motor (50) to the housing (20).

11 Claims, 6 Drawing Sheets

(56) References Cited

U.S. PATENT DOCUMENTS

| | | | |
|---|---|---|---|
| 5,974,615 A * | 11/1999 | Schwarz-Hartmann | A61C 17/3472 15/22.1 |
| 6,422,867 B2 * | 7/2002 | Lang | A61C 15/047 132/322 |
| 7,067,945 B2 * | 6/2006 | Grez | A61C 17/3418 15/22.1 |
| 7,627,922 B2 | 12/2009 | Miller et al. | |
| 2011/0239383 A1 * | 10/2011 | Nishiura | A61C 17/3445 15/22.1 |

FOREIGN PATENT DOCUMENTS

| | | |
|---|---|---|
| JP | 2005261462 A | 9/2005 |
| WO | 2013141359 A1 | 9/2013 |

\* cited by examiner

SUSPENDED MOTOR MOUNTING SYSTEM IN A POWER TOOTHBRUSH

CROSS-REFERENCE TO PRIOR APPLICATIONS

This application is the U.S. National Phase application under 35 U.S.C. §371 of International Application No. PCT/IB2015/051220, filed on Feb. 18, 2015, which claims the benefit of U.S. Provisional Patent Application No. 61/980,207, filed on Apr. 16, 2014. These applications are hereby incorporated by reference herein.

Aspects of this invention relate generally to motor-driven powered toothbrushes. More particularly, the invention relates to toothbrush features which promote greater durability and control of vibrations transmitted to the user through the toothbrush handle.

Power toothbrushes are in general well known and encompass a wide variety of designs and physical arrangements. Many power toothbrushes have a rotary-type motion. Some have the capability of a 360° armature rotation, but due to design arrangements produce an oscillatory movement limited to a particular range of motion, i.e. a selected arcuate portion of 360°, in order to provide a more suitable brushing effect. Some of these rotary motion devices are mechanically driven, while others are resonant systems, involving a movable mass such as a brushhead structure and a spring which is attached to the handle. In a resonant system, the brushhead is driven at a frequency relatively close to the natural frequency of the system.

There are a number of ways to implement a resonant toothbrush. Resonant power toothbrushes may use a motor with a swinging armature, such as those described in co-assigned U.S. Pat. No. 5,189,751. A more recent resonating toothbrush design involves a drive with a brushhead end and an armature end separated by a fixed nodal spring, such as one described in co-assigned U.S. Pat. No. 7,627,922. The former type uses an armature that transmits much of the device's vibration to the user through the toothbrush housing. The latter design sought to mitigate the vibration and shock by operating at a near-resonant frequency in which the brushhead rotates 180° out of phase from the rotation of the armature. Thus, the drive assembly is substantially isolated vibrationally from the housing.

Each of these designs has been discovered to clean the teeth optimally through a narrow combination of dynamic parameters. The optimal combination is described in U.S. Pat. No. 5,378,153 as a triangular region of brushhead frequencies and motion amplitude, where amplitude is further driven by the size of the brushhead and the amplitude of shaft rotation. U.S. Pat. No. 7,067,945 describes the parameter as the amplitude of the angular rotation of the toothbrush shaft, which is stated there to be about 11 degrees with that brushhead geometry.

Even more recent is a resonating toothbrush having a floating rotor drive system. An example of this design is described in co-assigned U.S. Pat. No. 7,876,003. The motor in such a system may be arranged similarly to a rotational motor, but is driven such that the shaft oscillates about its axis, i.e. rotational oscillation, and optionally along its axis, i.e. axial oscillation. The "spring" in this type of design is the permanent magnet assembly in the stator, which draws the poles of the rotor back into the neutral magnetic position in the absence of a driving signal.

Several problems arise in the resonating toothbrush of the design described in the '003 patent. First, plastic injection-molded parts are commonly used in the frames. These frame parts are necessary to hold the internal functional parts together (i.e. battery, charge coil, printed circuit board assembly, drive system, seal, etc.) Existing frames are comprised of several injection-molded parts with separate functions. Resonant drive systems also use such multi-part frames in order to hold the drive system, PCBA, battery, and charge coil with one plastic injection-molded part. The system also uses an additional part to create a seal seat for sealing the drive shaft to the housing in order to prevent water-ingress. Such designs are not exclusive to products using resonant drive systems, but also in use with other reciprocating or sweeping motion power toothbrushes as well as other hand-held personal devices needing sealing surfaces for both face-seals and radial seals. Thus, there is a need to reduce vibration and sound through isolation of the moving parts in a less-expensive and more effective system.

Another problem which arises in floating rotor designs is that of cogging. Cogging is the slipping of a rotor pole from one permanent magnet alignment to an adjacent permanent magnet. The slipping may occur as a result of an external stress such as shock or applied mechanical force. The result of slipping is an undesired at-rest position of the shaft and associated driven brushhead, in an undesired rotational position, an undesired axial position, or both.

Yet another problem which arises is that existing frame designs are too expensive. There is a need to reduce cost by creating modular parts that mate with the frame, each part having several complex functions. Especially desired is a system of low-cost parts which improve the durability of the device by absorbing axial shocks. Axial shocks can, for example, be experienced if the toothbrush is dropped on the end of its shaft. A secondary desired result for these features is lower material and assembly costs.

The present invention provides a solution to the deficiencies in the prior art through the introduction of a single-part frame design that incorporates an elastomeric clamp on the motor. Whereas the motor is the main vibration creation mechanism in the system, the invention innovatively addresses the problem of vibration isolation. In particular, the present invention relies upon the use of an elastomeric material attached to a plastic injection-molded frame. The incorporated design features allow the motor to be mounted between two areas of elastomer. Combined with a magnetically suspended shaft, with minimal contact on bearings, the majority of the vibration energy is directed into the elastomeric material where it dissipates before reaching the housing where it can be transferred to the user.

In one embodiment of the invention, a system for mitigating mechanical shock in a power toothbrush is described. The system comprises an elongated housing open at a distal end and a proximal end, and a frame slideably disposed within the housing, the frame having a distal end and a proximal end. A motor is disposed within the frame, the motor including a floating shaft, the floating shaft having a distal end extending through the frame and housing and a proximal end extending within and toward the frame proximal end. A resilient motor mount is disposed within the frame adjacent the motor, the motor mount including a compression surface for holding the motor in the frame and a bottom bumper spaced away from the proximal end of the shaft. The system also includes a multi-function charging coil bobbin disposed in resilient contact with the proximal end of the frame at the housing proximal end, wherein the charging coil bobbin is further engaged with an inside wall of the housing proximal end in an arrangement which compressibly biases the frame against the housing distal end. The arrangement of elements act in concert to absorb axial shocks applied along the longitudinal axis of the toothbrush, and in particular to absorb shocks applied to the shaft end of the toothbrush.

According to another aspect of the invention, a system for damping vibration in a power toothbrush is described, comprising an elongated housing open at a distal end and a proximal end and a frame slideably disposed within the housing, the frame having a distal end and a proximal end. A resonating motor is disposed within the frame, the motor including a floating shaft, the floating shaft having a distal end extending through the frame and housing and a proximal end extending within and toward the frame proximal end. A resilient motor mount is disposed within the frame adjacent the motor, the motor mount including a compression surface for holding the motor in the frame. A top bumper is disposed between the motor and the frame distal end, wherein the motor mount and top bumper are arranged to damp rotational resonating vibration between the motor and the housing. Additional elements are described which further improve the damping features, including a coil bobbin and a shaft seal which act in concert to provide damping between the frame and the housing.

Figure 1:
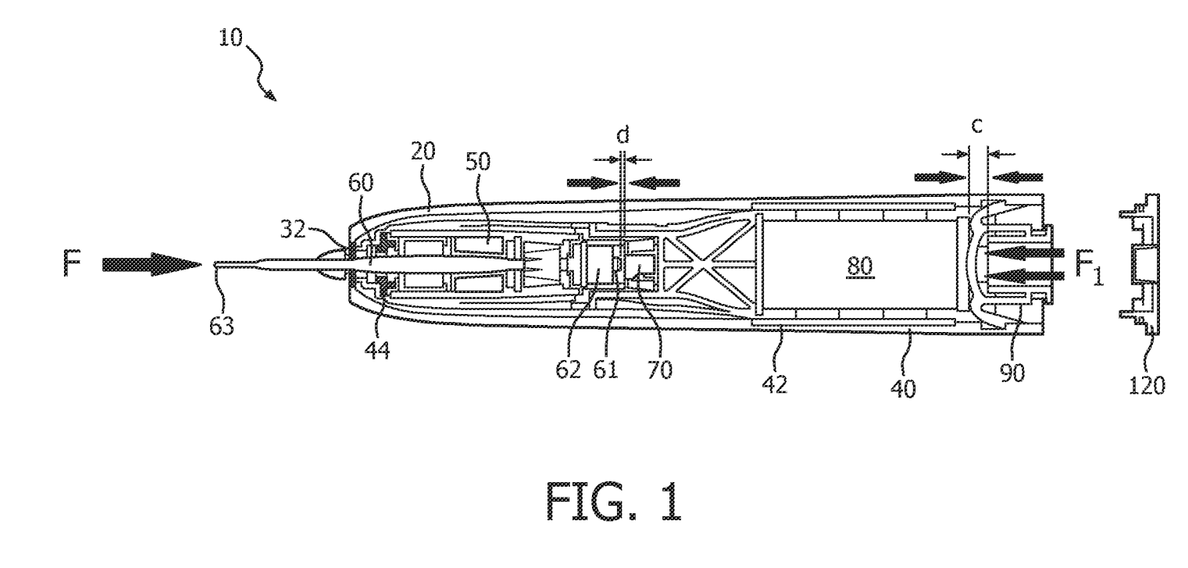
FIG. 1 illustrates a power toothbrush assembly, including a system for mitigating shock and vibration, according to one embodiment of the invention.

Now turning to the Figures, FIG. 1 illustrates an assembly for a power toothbrush 10, including a system for mitigating mechanical shock and for damping vibration, according to one embodiment of the invention.

Most components of the power toothbrush 10 are contained within an elongated housing 20 that is preferably sized to fit comfortably in a human hand. Preferably of a rigid and lightweight plastic, the housing 20 protects and seals internal components from shock and water ingress. Housing 20 includes opening at the distal end, i.e. an end showing a shaft distal end 63, and an opening at a proximal end, i.e. an end showing an end cap 120.

Arranged within housing 20 is a frame 40. Frame 40 is configured to hold most of the remaining system components, each of which are described in more detail below. Frame 40 may also be constructed of a lightweight rigid or semi-rigid plastic.

Frame 40 is disposed with one or more frame rails 42 which mate with corresponding slots along the interior walls of housing 20 along its longitudinal axis. The rails 42 allow for easy insertion of the frame 40 into the housing proximal end during assembly. The distal and proximal ends of frame 40 correspond respectively with the housing 20 distal and proximal ends.

Nested within the frame 40 distal end is a motor 50. Motor 50 is preferably a resonant motor having a floating shaft 60 that is suspended axially and rotationally within the motor by means of a permanent magnetic field. The field is preferably established with permanent magnets arranged within the motor housing. Motor shaft distal end 63 is arranged to extend through the frame 40 and housing 20 distal end, distal end 63 being shaped to receive a brushhead or other appliance.

The motor shaft 60 is arranged to also extend through the motor casing toward the frame proximal end. Shaft proximal end 61 preferably includes a shaft pawl 62, the function of which will be described in more detail below.

Motor 50 is held within frame 40 by two components, a motor mount 70 and a top bumper 44. A resilient motor mount 70, preferably constructed of an elastomeric material is disposed at the proximal end of the motor between motor 50 and frame 40. As will be described in more detail, the motor mount 70 is arranged to be axially spaced away from the shaft proximal end 61 by a distance d when the power toothbrush 10 is assembled. Motor mount 70 provides axial shock protection in the device, such as that induced by a force on the shaft distal end 63 shown at F.

During operation, motor 50 will tend to pass vibration through to the housing 20. Vibrations may be in the shaft rotation direction as the shaft oscillates, or in the axial directions as the shaft displaces along its axis. These vibrations will be passed to the user's hand through the housing unless damped or mitigated.

Compressed between the distal end of the motor 50 and the distal end of the frame 40 is top bumper 44. Top bumper 44 is preferably constructed of a resilient elastomeric material that is suitable to damp vibration from the motor and to protect the internal components from external shock.

Mount 70 and top bumper 44 also act in concert to damp rotational resonating vibration between the motor and the housing.

Compressed between frame 40 and housing 20 at the distal end is a shaft seal 32. Shaft seal 32 also substantially surrounds the shaft 60. The main function of the shaft seal 32 is to prevent water ingress along the shaft 60 and distal end of housing 20. However, shaft seal 32 also performs a secondary function of damping vibration, including resonating vibration from the motor.

Figure 2:
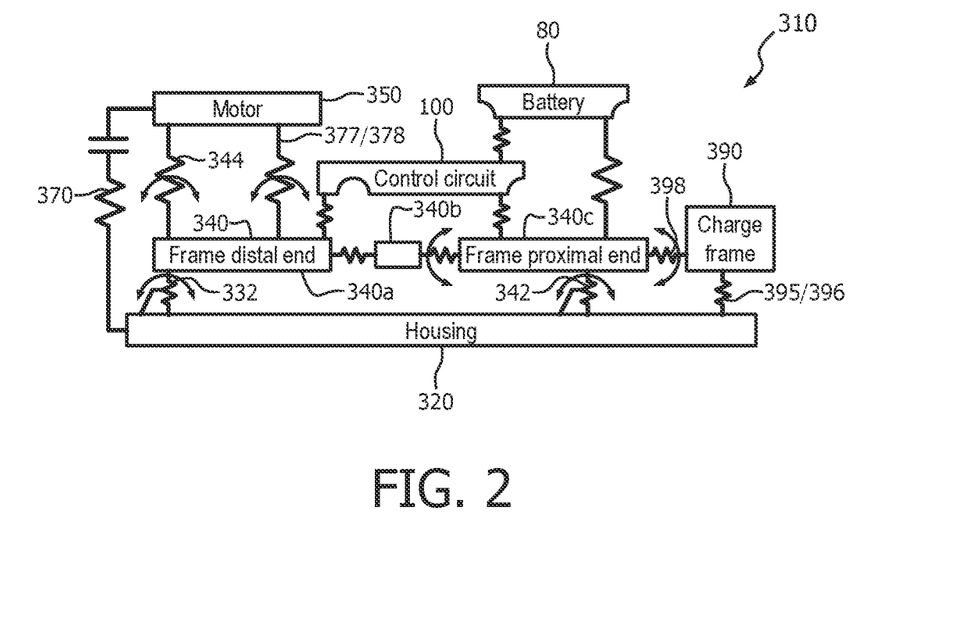
FIG. 2 illustrates an equivalent spring mass diagram of a power toothbrush assembly, according to another aspect of the invention.
Figure 5:
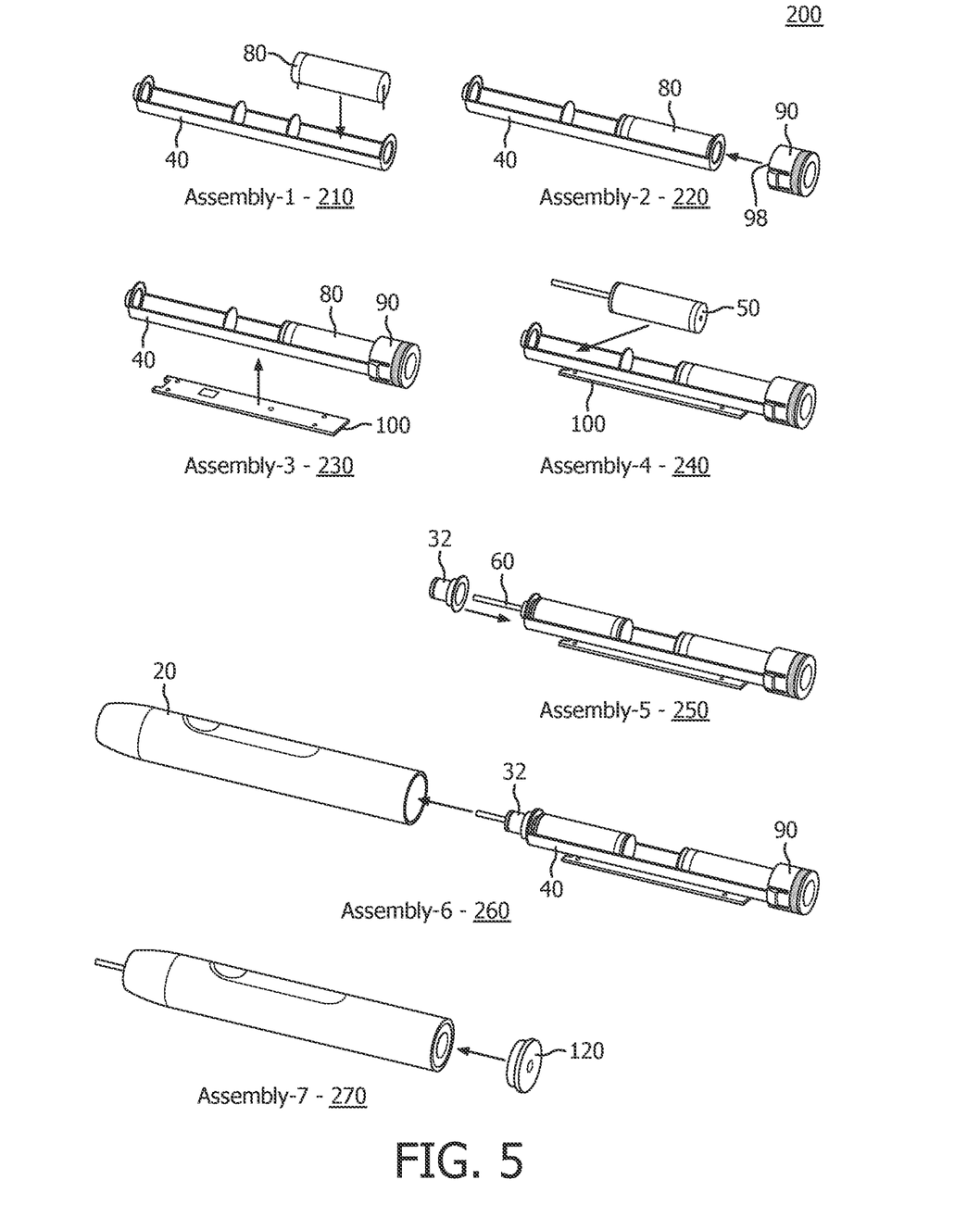
FIG. 5 illustrates a method of the successive steps of assembling a power toothbrush, according to yet another embodiment of the invention.

FIG. 1 also shows one or more rechargeable batteries 80 disposed in the frame 40 near the proximal end of the housing. A control circuit board 100 which may be mounted on frame 40 is shown in FIGS. 2 and 5.

Arranged proximal to battery 80 is a multifunction charging coil bobbin 90. Bobbin 90 receives a conductive winding which facilitates inductive charging of the rechargeable battery 80. Bobbin 90 also has features, e.g. a bridge spring 98, shown in FIGS. 4A through 4C, described following, which cushions against axial shock and provides tolerance mitigation during assembly. The forces applied by bobbin 90 are generally shown as "F1" in FIG. 1. Bobbin 90 also is constructed to hold the frame 40 within housing 20, such that frame 40 is substantially vibrationally isolated from housing 20.

Charging coil bobbin 90 is arranged to reside in resilient contact with the proximal end of the frame 40. As shown in FIG. 1, and as will be described in more detail below, relating to FIGS. 4A through 4C, bobbin 90 may be compressed up to a maximum compression dimension "C" to perform its protective/tolerance functions. Also as shown in more detail in FIGS. 4A through 4C, bobbin 90 is further engaged to the inside wall of the housing 20 proximal end by means of tabs and slots or equivalent, such that the bobbin 90 compressibly biases the frame 40 and/or shaft seal 32 against the housing 20 distal end.

End cap 120 is disposed onto the proximal end of housing 20 to protect the internal components from shock and water ingress.

Although the assembly in FIG. 1 is shown as linear, some embodiments may include a drive shaft that is positioned at a selected angle away from the longitudinal axis of the housing, which allows for optimal placement of the brushhead in the mouth.

FIG. 2 illustrates a system spring mass equivalent 310, equivalent to the assembly shown in FIG. 1. Equivalent 310 is presented to further illustrate the benefits of the assembly. Mass components are shown as follows: Housing mass 320 includes the housing 20 but can also include the user's hand. Frame mass 340 is shown in three parts for the purposes of illustrating its internal resilience: a frame distal end 340a, a middle 340b and a proximal end of the frame 340c. Control circuit 100 and battery 80 are shown, but are not particular to the system spring mass equivalent. Motor mass 350 corresponds to motor 50. Charge frame mass 390 corresponds to charging coil bobbin 90.

Spring equivalents are shown as follows. Top bumper rotational damping and axial resilience are shown at top bumper spring 344. Motor mount 70 is shown having a first and second mount arm spring 377, 378 at the proximal end of the motor 350. Springs 377/378 also provide rotational damping and axial resilience between motor 350 and frame 340.

Shaft seal spring 332 provides additional rotational damping and axial resilience from/to the motor between the frame 340 and the housing 320. The frame rail spring 342 also provides some rotational damping and axial resilience between frame proximal end 340c and the housing 320 due to the inherent resilience in the frame structure between the elastomeric motor mounts and the frame rail, and also from within the frame rail mounting structure itself, which may include some elastomeric damping material.

Rotational damping and axial resilience is provided between the proximal end of the frame 340c and the charge frame mass 390 by a bridge spring equivalent 398. Bridge spring equivalent 398 corresponds to e.g. the bridge spring 98 portion of charging coil bobbin 90. Finally, the connecting structure between charge frame 390 and housing 320 provides a spring function at housing connect springs 395, 396.

As can be seen in FIG. 2, vibrations induced by motor mass 350 may be isolated from the frame at top bumper 344 and motor mount arms 377, 378. Secondarily, the vibrations from the frame may be isolated from the user's hands at shaft seal spring 332, bridge spring equivalent 398, and frame rail spring equivalent 342, as well as through the bobbin 90 at first and second housing connect springs 395, 396.

Another spring equivalent, motor mount spring 370 between the motor 350 and housing 320 masses provides axial shock protection when the motor shaft is displaced greater than the distance "d" to the motor mount 70 as shown in FIG. 1. Motor mount spring 370 corresponds to a bottom bumper 71, explained in further detail below, that is disposed on motor mount 70. Under this condition of axial force, the motor mount and bridge spring equivalents 370, 398 act in concert to absorb further axial shock originating from the floating shaft proximal end 61.

An alternate source of external force F may be applied in situations where a user is fitting a brushhead onto shaft distal end 63. Such an applied force will tend to displace the floating shaft through motor 50, and by extension, frame 40 through housing 20. In this situation, the bottom bumper and bridge spring equivalents 370, 398 act in concert to resist the applied axial force. The sum of the spaced away distance "d" and the maximum compression distance "C" in this case should be less than the equivalent spring compression distance that is required to attach the brushhead onto the shaft. This allows the brushhead to be fitted without causing pole failure within the motor 50.

Figure 3A:
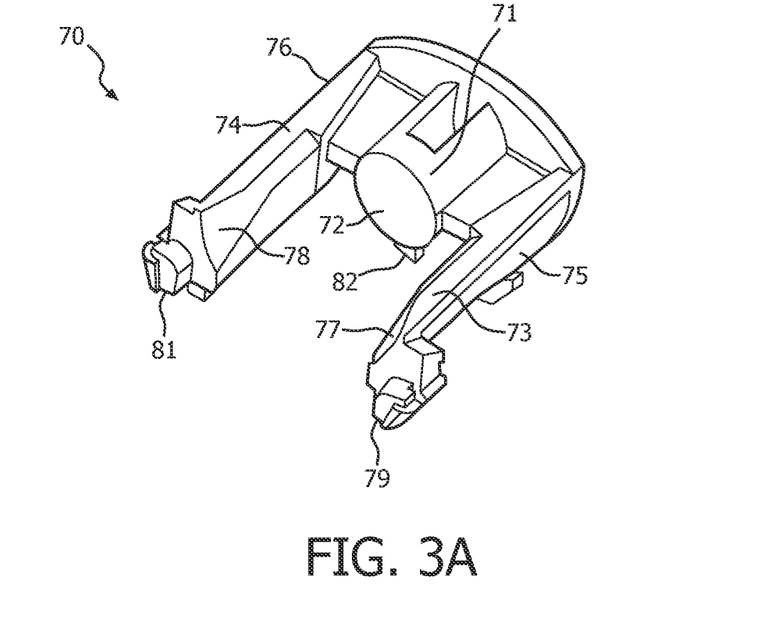
FIGS. 3A, 3B, and 3C illustrate a resilient motor mount for a resonating motor in a power toothbrush, according to another embodiment of the invention.
Figure 3B:
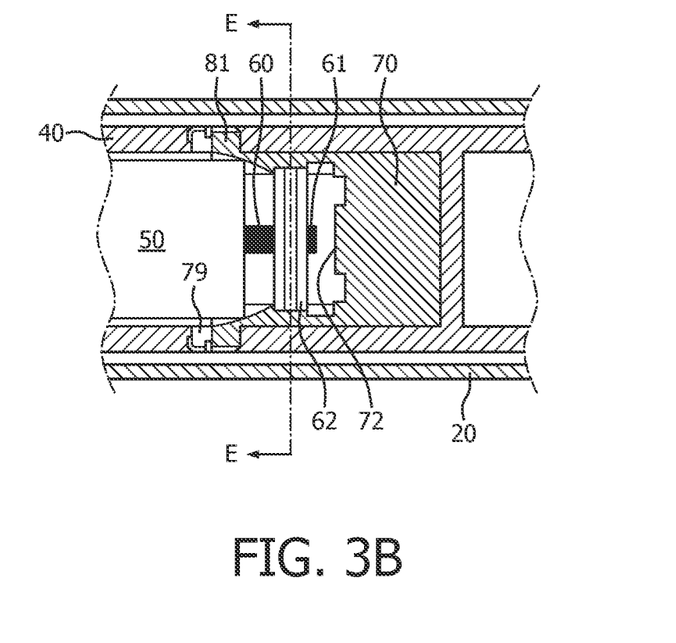
Figure 3C:
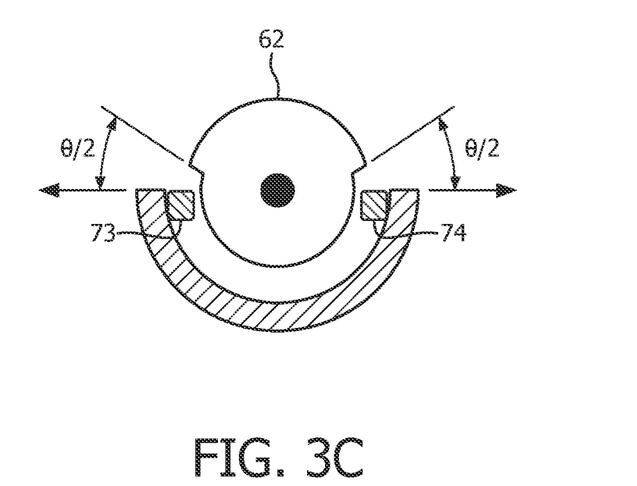

Now turning to FIGS. 3A, 3B, and 3C, there is illustrated particular embodiments of the resilient motor mount 70 for a resonating motor 50 in a power toothbrush. Motor mount 70 is particularly characterized by having features which are arranged to limit a maximum displacement of the associated shaft 60, in either of a rotational displacement or along the shaft axis. Motor mount 70 is also disposed to be in a compressive arrangement between the motor 50 and a side surface of either of the frame 40 or the housing 20.

The embodiment shown in FIG. 3A is a resilient motor mount 70 having a bottom bumper 71 and first and second mount arms 75, 76. Bottom bumper 71 further includes a an axial stop surface 72, which is disposed in a spaced away facing orientation to the shaft proximal end 61. Bottom bumper 71 functions to limit the axial displacement of the proximal shaft end 61, and to absorb energy from the shaft end 61 striking the bumper 71, as shown in FIG. 3B.

Mount arms 75, 76 are disposed in a compressive arrangement between the motor 50 and a side surface of frame 40. Each of the mount arms 75, 76 includes at least one compression surface 77, 78 disposed between mount 70 and frame 40, which is shaped to receive a portion of the motor 50 proximal end.

For descriptive purposes, bottom bumper 71 has a central axis and a periphery, the central axis generally aligned perpendicular to and passing through the center of stop surface 72. In the illustrated embodiment shown in FIGS. 3A and 3B, first and second mount arms 75, 76 are disposed outside of the periphery and extending away from the periphery in a direction along the central axis. Mount arms further includes a first and second cogging stop surface 73, 74 and a mount tab 79, 81. An additional mount tab 82 may be included on bottom bumper 71. At least one mount tab 79, 81, 82 on motor mount 70 may engage in corresponding slots in frame 40 to prevent the mount 70 and motor 50 from rotating within the frame 40. As can be seen, the resulting resilient motor mount 70 is generally u-shaped and of a unitary piece of elastomeric material, such as rubber or plastic.

First the axial stop surface 72 is disposed in a spaced away distance "d" from the shaft proximal end 61 as shown in FIG. 1. This arrangement allows for free rotation and axial vibration for normal toothbrush operation without undue friction losses. Under axial shock or excessive force however, the bottom bumper 71 and proximal shaft end 61 come into contact, which opposes further displacement of the shaft 60 in the axial direction. Such displacement can be induced by dropping the toothbrush or by excessive force in pressing a brushhead onto its distal shaft end 63. In the latter case, the spaced away distance should be less than a displacement that is caused by the operation of receiving the brushhead onto the shaft. Alternatively, the spaced away distance "d" should be smaller than a pole-slipping distance from the axial magnetic rest position to prevent axial pole slippage. Alternatively, the spaced away distance "d" should be smaller than a distance between a pole element on the shaft 60 and a back end casing surface of the motor, to prevent motor damage.

Mount tabs 79, 81, and 82 prevent the rotation of the resilient motor mount 70 within the frame 40 during operation, Corresponding slots in frame 40, or alternatively housing 20, receive the tabs 79, 81 such that the engagement prevent the rotation displacement. In the FIG. 3 embodiments, tabs 79, 81 are arranged generally opposite compression surfaces 77, 78 on the mount arms 75, 76. Tab 82 is located at the base of bottom bumper 71.

The resilient motor mount 70 includes cogging stop surfaces 73, 74 that are disposed at a radial distance from the shaft axis. Cogging stops 73, 74 interact with the shaft pawl 62 disposed on the shaft proximal end 61 in conditions of excessive force to prevent excessive rotation of the shaft. By limiting the rotational displacement of the shaft, the cogging stops 73, 74 also prevent a permanent cogging rotational displacement where the shaft pole skips to the next stator magnet position.

As illustrated in the section view of FIG. 3B at FIG. 3C, the cogging stops 73, 74 are arranged at an angular displacement from shaft pawl 62. During normal resonating operation, such as up to a total displacement of 11 degrees, no contact will occur between stops 73, 74 and pawl 62. However, the stops will prevent additional angular motion beyond a limit θ(theta)/2 in either direction induced by, for example, forced twisting of the shaft on the appliance.

Figure 4A:
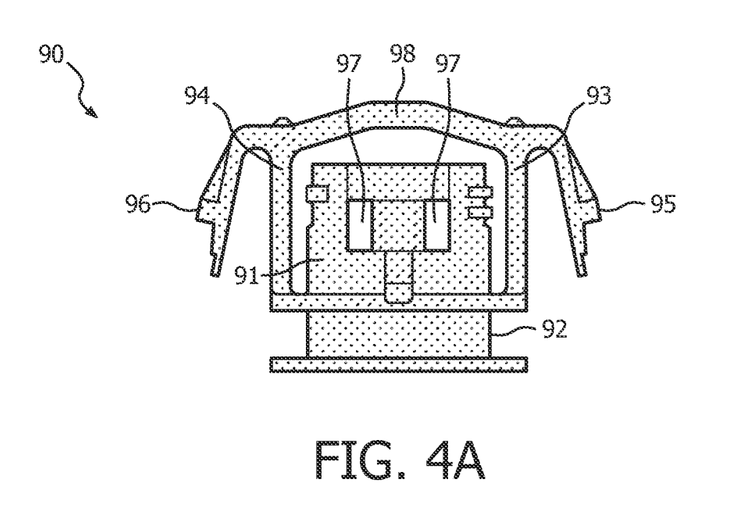
FIGS. 4A, 4B, and 4C illustrate a multi-function charge coil bobbin for a power toothbrush, according to another embodiment of the invention.

FIG. 4A illustrates a multi-function charging coil bobbin 90 according to one embodiment of the invention. Bobbin 90 includes a bobbin body 91, which in this embodiment is a generally hollow cylindrical shape. For illustrative purposes, bobbin body 91 has a central axis generally aligned with the longitudinal axis of housing 20. A coil winding surface 92 is disposed at the proximal end of bobbin 90, which is arranged to receive a winding of conductive wire sufficient to permit inductive charging of rechargeable battery 80. The particular coil winding surface can vary in size in order to accept different wire diameters and types. Not shown is that the winding is disposed in electrical communication with the battery 80 via control circuit 100, which in this case performs a function of a charging control circuit. Bobbin body 91 provides structural integrity in a flexible arrangement, so it should be constructed of a durable and flexible material. Preferably low cost and unitary, the material can be a durable and resilient material such as plastic, ABS (acrylonitrile butadiene styrene), or the like, that can be molded.

Figure 4B:
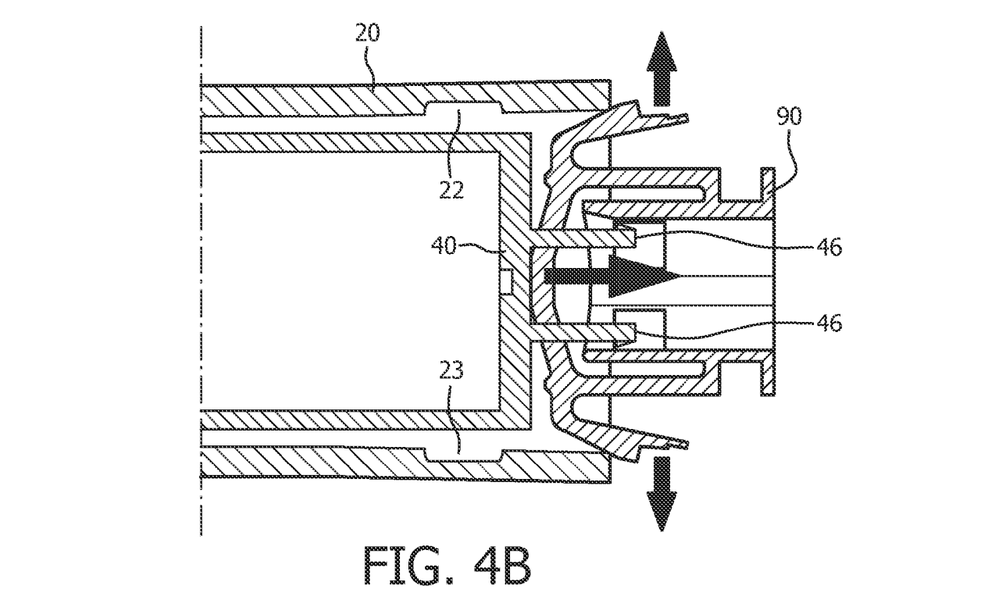

Bobbin 90 further includes first and second housing connect tabs 95, 96. Tabs 95, 96 are arranged to fixedly engage to corresponding slots 22, 23 on an interior surface of the housing 20 proximal end, as shown in FIG. 4B. Alternatively but not shown, the slots and tabs on each element could be exchanged, staying within the scope of the invention.

Spaced away from a distal end of the bobbin body 91 and across its central axis is a bridge spring 98. Bridge spring 98 is preferably arched as shown, whereas the top center of the arch is spaced away from the top of the body 91. The arrangement allows for a maximum compression travel between arch and body, exemplified by the dimension "C" in FIG. 1. Overall, the bridge spring 98 is sized to absorb axial shocks that originate from the distal ends of the frame 40 and housing 20.

Each end of bridge spring 98 is flexibly connected to body 91 by a respective first and second housing connect arm 93, 94. Each housing connect arm 93, 94 may be connected to the side of body 91, preferably near a body end substantially opposite the bridge spring 98. As shown in FIG. 4A, each arm 93, 94 may be disposed in a spaced away relationship from body 91 and generally in parallel to the body's central axis. This arrangement allows for additional flexibility and travel of the bridge spring 98 during operation.

Tabs 95, 96 are also preferably connected to a respective connect arm 93, 94 at each respective end of bridge spring 98, as shown in FIG. 4A. In order to facilitate easy slideable insertion and assembly of the bobbin 90 into the housing 20, each connect tab 95, 96 is arranged folded over to an acute angle with the central axis, and directed toward the proximal end of bobbin body 91.

Bobbin 90 also includes one or more frame connect slots 97 disposed in body 91. Frame connect slots 97 are arranged to receive a corresponding bobbin connect tab 46 of frame 40 in compressible engagement. Charging coil bobbin 90 is arranged to reside in resilient contact with the proximal end of the frame 40 by means of compression pressure and the frame bobbin connect tabs 46.

FIG. 4B illustrates another view of the multi-function charging coil bobbin 90, including how the coil installably interacts with the housing 20 and frame 40. Bobbin 90 is shown connected to frame 40 by means of engagement of frame bobbin connect tabs 46 into frame connect slots 97. When connected as shown, bridge spring 98 is disposed in resilient compression contact with frame 40. The connection between slot 97 and corresponding bobbin connect tab 46 is maintained by the resilient compression from the bridge spring 98 pressing the bobbin body 91 and slot 97 away from the frame 40.

Figure 4C:
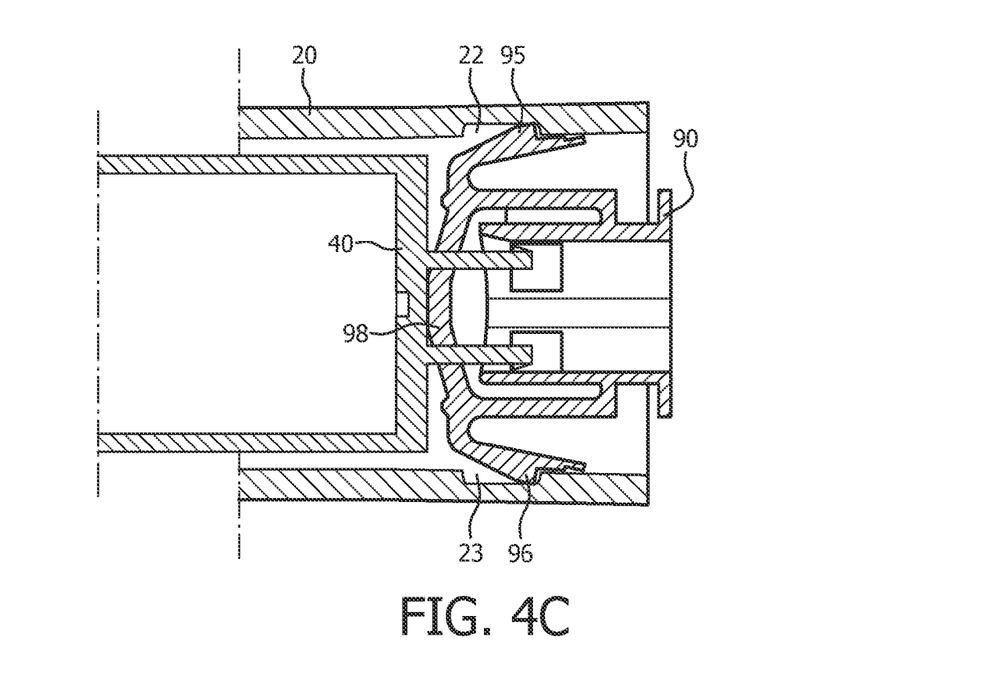

As shown in FIG. 4C, the housing 20 further includes corresponding slots 22, 23 on an interior surface of the proximal end. The slots are disposed to mate securely with the tabs 95, 96 when the bobbin 90 is fully inserted into the housing 20.

It can be seen in FIG. 4C that by the arrangement of bridge spring 98 and tabs 95, 96 with respect to the body, the compression flexure of bridge spring 98 induces a reaction force on tabs 95, 96 in the proximal and outward directions, i.e. toward the interior surface of the housing 20. Such a result is beneficial because in the event of axial shock in the device, the tabs 95, 96 will be pressed more forcefully into the housing. The bobbin 90 will thus be less likely to dislodge from the housing.

It can also be seen in FIGS. 1 and 4B that the compression distance "C" of bridge spring 98 is somewhat influenced by the respective geometries of the frame 40, housing 20 and shaft seal 32. Bridge spring 98 thus functions to mitigate minor tolerance errors between and within these components. Also, by acting as a "float" for frame 40 within the housing 20, bridge spring 98 also mitigates pressing forces on the motor shaft 60 due to the insertion of a brushhead onto the shaft distal end 63. Bridge spring 98 can fulfill these functions until it is compressed to its maximum extent "C" as shown in FIG. 1.

Now turning to FIG. 5, a method 200 of assembling a power toothbrush is described, which in particular highlights the benefits of the combined components. Assembly begins by the steps of inserting and attaching sub-components to a frame 40. Battery 80 is inserted at step 210. Coil bobbin 90 is attached to the proximal end of frame 40 at step 220, where the parts are resiliently held in contact by means of bridge spring 98. The control circuit 100, on a printed circuit board assembly, is installed on the frame 40, after which the coil bobbin 90 winding is electrically connected to the control circuit 100. Battery 80 is also connected to the control circuit 100. Frame 40 assembly is completed at step 240 by mounting the motor 50 into the distal end of the frame 40, and electrically connecting the motor to the control circuit 100. At step 250, a shaft seal 32 is installed over the distal end of the frame 40 and around the motor shaft 60. In each of the frame assembly steps, the motor mounts 70 and bumpers 44, along with other vibration isolating material, may be installed prior to or with the sub-components.

A housing 20 open at both ends is then provided at step 260, whereupon the internal assembly of frame 40 and subcomponents is inserted into the proximal end of the housing 20. The frame 40 may slide on rails inside the housing 20 during insertion. Insertion is complete when the connect tabs or slots on the charging coil bobbin snap into and engage the corresponding slots or tabs on the housing. At completion of step 260, the bobbin bridge spring 98 provides a resilient contact between housing 20 and frame 40 proximal ends to bias the shaft seal 32 against the housing 20 distal end. It can be seen that the resilient contact also provides mitigation for tolerance errors in the assembly.

Assembly is completed when end cap 120 is snapped onto the proximal end of the housing 20.

The advantages afforded by this assembly method include reduced cost. The method reduces cost for the reason that the parts can be made in bulk apart from the assembly line, and then installed only when needed. For example, the coil bobbin 90 can be wound with a conductive coil apart from and prior to the device assembly, and brought to the assembly location only when needed.

The contemplated scope of the inventions that are described here pertain to various modifications as well. Minor changes to the geometry of the motor mount 70 and coil bobbin 90 in particular fall within the claimed scope, as long as the geometry fulfills the described functions and advantages.

What is claimed is:

1. A system for mitigating mechanical shock in a power toothbrush, comprising:
    an elongated housing open at a distal end and a proximal end;
    a frame slideably disposed within the housing, the frame having a distal end and a proximal end;
    a motor disposed within the frame, the motor including a floating shaft, the floating shaft having a distal end extending through the frame and housing and a proximal end extending within and toward the frame proximal end;
    a resilient motor mount disposed within the frame adjacent the motor, the motor mount including a compression surface for holding the motor in the frame and a bottom bumper spaced away from the proximal end of the shaft;
    a multi-function charging coil bobbin comprising a bridge spring having two ends, the bridge spring disposed across and in a spaced away disposition from a proximal end of the bobbin, the mufti-function charging coil bobbin disposed in resilient contact with the proximal end of the frame at the housing proximal end, wherein the charging coil bobbin is further engaged with an inside wall of the housing proximal end in an arrangement which compressibly biases the frame against the housing distal end, the bridge spring further disposed in resilient contact with the proximal end of frame).

2. The system of claim 1, wherein the floating shaft is suspended in an axial rest position within the motor with a permanent magnetic field.

3. The system of claim 2, wherein the spaced away distance is smaller than a pole-slipping distance from the axial rest position.

4. The system of claim 2, wherein the spaced away distance is smaller than a distance between a floating shaft pole element and a back casing surface of the motor.

5. The system of claim 1, wherein the housing and charging coil bobbin are fixedly engaged together by means of slots or tabs on an interior surface of the housing proximal end and corresponding tabs or slots disposed on each end of the bridge spring.

6. The system of claim 5, wherein the tabs or slots on each end of the bridge spring are arranged to displace toward the interior surface of the housing in response to a flexure of the bridge spring.

7. The system of claim 5, wherein the corresponding tabs or slots are arranged in a folded over configuration that enables a slideable engagement to the housing slots or tabs when the charging coil bobbin is inserted into the housing proximal end.

8. The system of claim 1, wherein the bridge spring is sized to absorb axial shock originating from the floating shaft distal end.

9. The system of claim 8, wherein the bridge spring has a maximum compression dimension, and further wherein the sum of the maximum compression dimension and a spaced away distance between the bottom bumper and the proximal end of the shaft is less than a compression distance required to attach a brushhead to the distal end of the shaft.

10. The system of claim 1, wherein the bottom bumper and the bridge spring are arranged to act in concert to absorb axial shock originating from the floating shaft distal end.

11. The system of claim 1, further comprising:
    a top bumper disposed in compression between the motor and the frame distal end; and
    a shaft seal disposed in compression between the frame distal end and the housing distal end and around the floating shaft distal end.

* * * * *